(12) United States Patent
Takatsuji et al.

(10) Patent No.: US 7,354,766 B2
(45) Date of Patent: Apr. 8, 2008

(54) MODIFICATION OF PLANT CROSSING PROPERTIES VIA GENE TRANSFER

(75) Inventors: Hiroshi Takatsuji, Ibaraki (JP); Ken-ichi Kubo, Nara (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 0 days.

(21) Appl. No.: 11/250,098

(22) Filed: Oct. 12, 2005

(65) Prior Publication Data

US 2006/0101538 A1 May 11, 2006

(30) Foreign Application Priority Data

Oct. 15, 2004 (JP) .............................. 2004-301043

(51) Int. Cl.
*C12N 15/82* (2006.01)
(52) U.S. Cl. ..................................... 435/468
(58) Field of Classification Search ............. None
See application file for complete search history.

(56) References Cited

FOREIGN PATENT DOCUMENTS

| AU | 779285 | | 6/2001 |
| CA | 2374375 | * | 11/2000 |
| JP | 2001-145429 | | 5/2001 |
| JP | 2001-145430 | | 5/2001 |
| JP | 2003-092936 | | 4/2003 |
| JP | 2003-092937 | | 4/2003 |
| WO | WO 0071704 A1 | * | 11/2000 |
| WO | WO 01/37643 | | 5/2001 |
| WO | WO 01/37644 | | 5/2001 |

OTHER PUBLICATIONS

Keskin et al. (Protein Science, 13:1043-1055, 2004).*
Guo et al. (PNAS, 101: 9205-9210, 2004).*
Thornton et al. (Nature structural Biology, structural genomics supplement, Nov. 2000).*
Kubo et al. (NCBI, GenBank, Sequence Accession No. AB006597, pp. 1-2, Published Aug. 27, 1997).*
Kapoor et al. (The Plant Cell, 14:2253-2367, Oct. 2002).*
Valvekens et al. (PNAS, 85:5536-5540, 1988).*
Kubo et al. (Plant Cell Physiol., 41:377-382, 2000).*
Dale et al. "Potential for the environmental impact of transgenic crops" (200) *Nature Biotechnology* 20(6):567-574.
Mariani et al. "Induction of male sterility in plants by a chimaeric ribonuclease gene" (1990) *Nature* 25(347):737-741.
Hiscock & Tabah, "The different mechanisms of porophytic self-incompatibility," *Phil. Trans. R. Soc. Lond. B*. (2003) 358(1434): 1037-1045.

* cited by examiner

*Primary Examiner*—David H. Kruse
*Assistant Examiner*—Vinod Kumar
(74) *Attorney, Agent, or Firm*—Foley & Lardner LLP

(57) ABSTRACT

An objective of the present invention is to genetically improve plant crossing properties as to effectively prevent recombinant genes in transgenic plants from spreading into the environment. A TFIIIA-type zinc-finger transcription factor gene ZPT2-10 was introduced into *petunia*. As a result, some of the transformants (i.e., transgene-dependent incompatibility (TDI) strain plants) were found to have a useful crossing property. Specifically, the plants were fertile and produced normal seeds when self propagated or mated with another specified transformant comprising the same recombinant gene, but were infertile (transgene dependent incompatibility) when mated with another transformant strain that does not have the TDI property or with a wild-type plant. It may be possible to utilize plants having such a crossing property to prevent transgenic plants from spreading into the environment.

3 Claims, 4 Drawing Sheets

MODIFICATION OF PLANT CROSSING PROPERTIES VIA GENE TRANSFER

CROSS-REFERENCE TO RELATED PATENT APPLICATIONS

Japan Priority Application 2004-301043, filed Oct. 15, 2004 including the specification, drawings, claims and abstract, is incorporated herein by reference in its entirety.

FIELD OF THE INVENTION

The present invention relates to plants imparted with transgene-dependent incompatibility upon ZPT2-10 gene introduction; agents and cells for producing the plants; and methods for producing the plants.

BACKGROUND OF THE INVENTION

In practical utilization of transgenic crops, there is concern that their recombinant genes may spread into the environment as a result of mating between wild-type and native species due to pollen dispersion. For example, crossing between herbicide-resistant transgenic crops and weeds may result in "superweeds", which acquire herbicide resistance and become irresponsive to pesticides (Dale, P. J. et al., Nat. Biotechnol. 20(6) 2002, 567-574). This problem is considered one of the critical problems that need to be solved for promoting public acceptance of transgenic plants from the standpoint of transgenic plant development and production. One of these strategies is utilization of male sterility, which has many examples (Mariani, C. et al., Nature 347, 1990, 737-741) including methods developed by the present applicant (Japanese Patent Application Kokai Publication No. (JP-A) 2001-145429 (unexamined, published Japanese patent application), JP-A 2001-145430, JP-A 2003-92936, and JP-A 2003-92937). However, it is difficult to apply male sterility methods to self-propagating crops, and there are problems such as inevitable mating by cross-pollination. In recent years, there are studies on methods for preventing the spreading of recombinant genes from pollens into the environment by incorporating recombinant genes into chloroplast genomes, which are thought to propagate only through maternal inheritance and not to be inherited via pollens.

SUMMARY OF THE INVENTION

The present invention was achieved in view of the above conditions. An objective of the present invention is to improve plant crossing properties for effectively preventing recombinant genes in transgenic plants from spreading into the environment. Specifically, an objective of the present invention is to provide plants that have acquired transgene-dependent incompatibility through genetic improvement, agents and cells for producing the plants, and methods for producing the plants.

In order to solve the aforementioned problems, the present inventors fused a potato-derived SK2 chitinase gene promoter with the TFIIIA-type zinc-finger transcription factor gene ZPT2-10, which is specifically expressed in the transmitting tissues of the *Petunia hybrida* style and introduced the SK2:ZPT2-10 into a *petunia*. The result showed that some of the resulting transformants [transgene-dependent incompatibility (TDI) strain] exhibit useful crossing properties.

The TDI-strain *petunia* is fertile and produces normal seeds if self propagated or mated with another transformant that comprises the same recombinant gene, and is however infertile when mated with a transformant strain that does not have a TDI property, or with a wild-type plant. That is, the TDI-strain *petunia* has transgene-dependent incompatibility. The crossing property of TDI strain transformants was observed in both cases where the TDI strain is used as a pollen parent or a pistil parent. Progenies inherit this phenotype along with the introduced SK2:ZPT2-10 gene; and when SK2:ZPT2-10 is lost by segregation, the normal crossing property recovers, thereby making the relation clear between the introduced gene SK2:ZPT2-10 and the phenotype.

The present invention is based on such unprecedented transgene-dependent incompatibility. More specifically, the present invention provides [1] to [6] as follows:

[1] an agent for imparting transgene-dependent incompatibility to a plant, wherein the agent comprises a DNA of any one of (a) to (d) or a vector comprising the DNA as an active ingredient:
  (a) a DNA encoding a protein comprising the amino acid sequence of SEQ ID NO: 2;
  (b) a DNA comprising the coding region of the nucleotide sequence of SEQ ID NO: 1;
  (c) a DNA encoding a protein comprising an amino acid sequence with one or more amino acid substitutions, deletions, additions, and/or insertions in the amino acid sequence of SEQ ID NO: 2; and
  (d) a DNA which hybridizes under stringent conditions to a polynucleotide comprising the nucleotide sequence of SEQ ID NO: 1;

[2] a plant cell capable of regenerating into a plant with transgene-dependent incompatibility, wherein a DNA of any one of (a) to (d) or a vector comprising the DNA is introduced into the cell:
  (a) a DNA encoding a protein comprising the amino acid sequence of SEQ ID NO: 2;
  (b) a DNA comprising the coding region of the nucleotide sequence of SEQ ID NO: 1;
  (c) a DNA encoding a protein comprising an amino acid sequence with one or more amino acid substitutions, deletions, additions, and/or insertions in the amino acid sequence of SEQ ID NO: 2; and
  (d) a DNA which hybridizes under stringent conditions to a polynucleotide comprising the nucleotide sequence of SEQ ID NO: 1;

[3] a plant with transgene-dependent incompatibility regenerated from the plant cell of [2];

[4] a plant with transgene-dependent incompatibility, which is a progeny or a clone of the plant of [3];

[5] a propagating material of the plant of [3] or [4]; and

[6] a method for producing a plant with transgene-dependent incompatibility, wherein the method comprises the steps of:
  (i) introducing a DNA of any one of (a) to (d) or a vector comprising the DNA into a plant cell:
    (a) a DNA encoding a protein comprising the amino acid sequence of SEQ ID NO: 2;
    (b) a DNA comprising the coding region of the nucleotide sequence of SEQ ID NO: 1;
    (c) a DNA encoding a protein comprising an amino acid sequence with one or more amino acid substitutions, deletions, additions, and/or insertions in the amino acid sequence of SEQ ID NO: 2; and (d) a DNA which hybridizes under stringent conditions to a polynucleotide comprising the nucleotide sequence of SEQ ID NO: 1; and (ii) regenerating a plant from the plant cell into which the DNA or the vector is introduced in step (i).

DETAILED DESCRIPTION OF THE INVENTION

Figure 1:
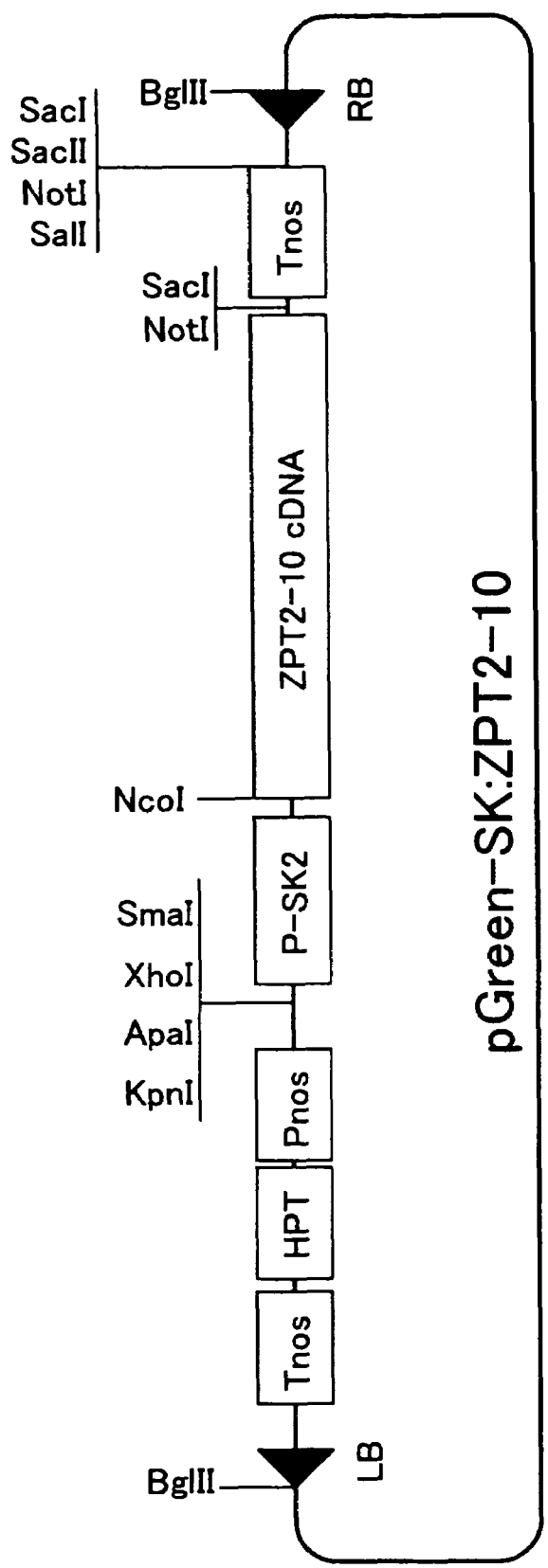
FIG. 1 shows the SK2:ZPT2-10 gene construct.

ZPT2-10 to provide agents that impart transgene-dependent incompatibility to plants.

In the present invention, the term "transgene-dependent incompatibility" refers to a crossing property that results in fertile plants producing normal seeds when self propagated or mated with a particular transformant comprising the same recombinant gene, and infertile plants when mated with a transformant strain that has no similar properties or with a wild-type plant.

Whether or not an agent comprising a certain gene imparts transgene-dependent incompatibility to a plant can be assessed as shown in Example 3. Specifically, whether a plant has the crossing property can be determined by examining whether a plant, to which a gene comprised in an agent is introduced, produces normal seeds when self-pollination occurs; and whether it fails to reach fruition when pollination occurs through mating with a wild-type strain.

In the present invention, the DNA comprised in an agent that imparts transgene-dependent incompatibility to plants is not particularly limited, and may be in the form of a cDNA or genomic DNA. Genomic DNAs and cDNAs can be prepared by using conventional means known to one skilled in the art. For example, the genomic DNA of ZPT2-10 can be prepared by designing an appropriate primer pair from the known nucleotide sequence (SEQ ID NO: 1) of ZPT2-10, performing PCR using genomic DNA prepared from a plant of interest as template, and screening genomic libraries using the resulting amplified DNA fragment as probe. Similarly, a cDNA encoding ZPT2-10 can be prepared by designing a primer pair as described above, performing PCR using cDNAs or mRNAs prepared from a plant of interest as template, and screening cDNA libraries using the resulting amplified DNA fragment as probe. The DNAs of interest may also be synthesized using a commercially available DNA synthesizer.

As active ingredients of the agents of the present invention, not only the DNAs that encode the *petunia*-derived ZPT2-10 protein (SEQ ID NO: 2), but also DNAs encoding proteins that are structurally similar to the protein (e.g., mutants, derivatives, alleles, variants, and homologs) can be used as long as they have the function of imparting transgene-dependent incompatibility to plants. Such DNAs include, for example, DNAs encoding a protein comprising an amino acid sequence with one or more amino acid substitutions, deletions, additions, and/or insertions in the amino acid sequence of SEQ ID NO: 2.

Examples of methods well-known in the art for preparing DNAs encoding a protein with altered amino acid sequence include site-directed mutagenesis methods (Kramer, W. and Fritz. H. J., Methods Enzymol. 154, 1987, 350-367). In nature, mutations in nucleotide sequences may also lead to mutations in the amino acid sequences of proteins encoded thereby. As described above, DNAs encoding a protein comprising an amino acid sequence with one or more amino acid substitutions, deletions, or additions in the amino acid sequence of the naturally-occurring ZPT2-10 protein (SEQ ID NO: 2) are included in the DNAs of the present invention, as long as they have the function of imparting transgene-dependent incompatibility to plants.

The number of amino acids to be altered is not particularly limited, but is generally 50 or less, preferably 30 or less, more preferably 10 or less (e.g., 5 or less, or 3 or less). Alterations of amino acids are preferably conservative substitutions. The hydropathic indices (Kyte, J. and Doolittle, R. F., J Mol. Biol. 157(1), 1982,105-132) and hydrophilicity values (U.S. Pat. No. 4,554,101) for each amino acid before and after an alteration are preferably within ±2, more preferably within ±2, and most preferably within ±0.5.

In addition, mutations in a nucleotide sequence are not always accompanied by mutations in the amino acids of the protein (i.e., degenerate mutations). Such degenerate mutants are also included in DNAs as active ingredients of the agents of the present invention.

DNAs encoding proteins that are structurally similar to the *petunia*-derived ZPT2-10 protein (SEQ ID NO: 2) can be prepared by using hybridization techniques (Southern, E. M., J Mol. Biol. 98(3), 1975, 503-517) and polymerase chain reaction (PCR) (Saiki, R. K. et al., Science 230, 1985, 1350-1354; and Saiki, R. K. et al., Science 239, 1988, 487-491). That is, DNAs of the present invention include DNAs that hybridize under stringent conditions to the DNA consisting of the nucleotide sequence of SEQ ID NO: 1. For isolating such DNAs, hybridization reactions are preferably performed under conditions of stringency. In the present invention, the term "stringent conditions" refers to the conditions of 6 M urea, 0.4% SDS, and 0.5×SSC, and hybridization conditions of equivalent stringency, without being limited thereto. Conditions of higher stringency such as 6 M urea, 0.4% SDS, and 0.1×SSC can be expected to isolate DNAs of higher homologies. A variety of factors such as temperature and salt concentration are considered factors that affect hybridization stringency. One skilled in the art can establish optimal stringencies by appropriately selecting these factors.

The DNAs isolated by the above-described hybridizations at the amino acid level are considered to have a high homology with the amino acid sequence of the *petunia*-derived ZPT2-10 protein (SEQ ID NO: 2). The term "high homology" refers to identities of at least 50% or more, more preferably 70% or more, most preferably 90% or more (e.g., 95%, 96%, 97%, 98%, 99%, or more) over the entire amino acid sequence. Amino acid sequence identities and nucleotide sequences identities can be determined by using BLAST algorithm (Karlin, S. and Altschul, S. F., Proc. Natl. Acad. Sci. USA 87(6), 1990, 2264-2268; and Karlin, S. and Altschul, S. F., Proc. Natl. Acad. Sci. USA 90(12), 1993, 5873-5877). BLASTN and BLASTX programs have been developed based on the BLAST algorithm (Altschul, S. F. et al., J. Mol. Biol. 215(3), 1990, 403-410). When nucleotide sequences are analyzed using BLASTN, parameters are set to be, for example, score=100 and wordlength=12. When amino acid sequences are analyzed using BLASTX, parameters are set to be, for example, score=50 and wordlength=3. When BLAST and Gapped BLAST programs are used, default parameters for the respective program are used. Specific procedures of these analysis methods are publicly known.

DNAs which serve as an active ingredient in the agents of the present invention may be inserted into vectors. Vectors are not particularly limited, as long as they can allow introduced genes to be expressed in plant cells. For example, it is possible to use vectors comprising promoters for homeostatic gene expressions in plant cells (e.g., the promoter of the potato SK2 chitinase gene, the cauliflower mosaic virus 35S promoter, etc.), or vectors comprising promoters that are inducibly activated by external stimulation.

The term "agents" in the present invention may be the aforementioned DNAs or vectors into which the DNAs are inserted, and may be mixtures containing other components for use in the introduction into plant cells. For example, agents of the present invention include the aforementioned DNAs, vectors into which the DNAs are inserted, *Agrobacteria* into which the DNAs are introduced, and biochemical reagents and solutions comprising them.

Plants that demonstrate the transgene-dependent incompatibility can be produced by introducing into plant cells the aforementioned DNAs or vectors having the function of imparting transgene-dependent incompatibility to plants, and regenerating plants from the plant cells. Therefore, the present invention also provides methods for producing plants with transgene-dependent incompatibility.

The type of plant cells into which the aforementioned DNAs or vectors are introduced is not particularly limited as long as the transgene-dependent incompatibility can be imparted, and includes, for example, *petunia*, tobacco, tomato, and potato.

Plant cells into which the aforementioned DNAs or vectors are introduced are not particularly limited and may be in any form as long as they can be used to regenerate plants. For example, suspension-cultured cells, protoplasts, leaf discs, and calli can be used.

Introduction of the aforementioned DNAs or vectors into plant cells can be performed using methods known to one skilled in the art, such as polyethyleneglycol methods, electroporation, *Agrobacterium*-mediated methods, and particle gun bombardment. In the *Agrobacterium*-mediated methods, for example, according to the method by Nagel et al. (Nagel, R. et al. FEMS Microbiol. Lett. 67, 1990, 325-328), a DNA can be introduced into plant cells by introducing into *Agrobacteria* an expression vector to which the DNA is inserted, and infecting plant cells with the *Agrobacteria* via direct infection or by the leaf disc method.

Regeneration of plants from plant cells can be achieved according to the type of plants using methods known to one skilled in the art. For example, *petunia* shoots are regenerated on media containing auxin (indoleacetic acid (IAA)) and cytokine (benzylaminopurine (BAP)), and rooted and grown on media containing indolebutyric acid (IBA) (van der Meer I. M., Methods Mol. Biol. 111, 1999, 327-334). Torenia, tobacco, and gerbera plants can be regenerated by similar methods (Elomaa, P. et al., Plant J. 16, 1998, 93-99). Examples of methods for regenerating other plants include: Fujimura's method (Fujimura, T. et al., Plant Tissue Culture Lett. 2, 1985, 74-5) for rice; Shillito's (Shillito, R. D. et al., Bio/technology, 7, 1989, 581-587) and Gordon-Kamm's methods (Gordon-Kamm, W. J. et. al., Plant Cell. 2(7) 1990, 603-618) for corn; Visser's method (Visser, R. G. F. et al., Theor. Appl. Genet. 78, 1989, 594-600) for potato; Akama's method (Akama, K. et al., Plant Cell Reports, 12, 1992, 7-11) for *Arabidopsis thaliana*; and Dohi's method (JP-A Hei 8-89113) for Eucalyptus.

Once a plant transformed through the insertion of an aforementioned DNA or vector into its genome is obtained, it is possible to obtain progenies or clones from that plant by sexual or asexual reproduction. In addition, propagating materials (such as seeds, fruits, cuttings, tubers, tuberous roots, lines, calli, protoplasts, etc.) can be obtained from the plant, or progenies or clones thereof, and used for large-scale production of the plant.

The present invention provides plants with the above-described transgene-dependent incompatibility, plant cells which can be used to regenerate such plants, progenies or clones of such plants, as well as propagating materials of such plants.

The methods of the present invention can be used to prevent the above-described plant transformants from spreading into the environment. The present methods can be applied as a useful means to other plants for suppressing the spreading of transgenic plants into the environment and contribute to raise acceptance of the general public towards transgenic plants. In addition, the present invention can also be considered for use in the production of pure line seeds. In order to obtain high quality seeds retaining a pure line of a particular variety, methods of physical isolation, such as covering with bags after mating and producing seeds in isolated islands to which mediating insects cannot fly (Matsushima Chinese cabbage), are currently performed to prevent contamination by genes of other varieties. These methods are bound to face difficulties such as considerable amounts of labor and geographical restriction. However, when the present invention is put into practice, such physical isolation may become unnecessary.

Any patents, published patent applications, and publications cited herein are ZPT2-10 to provide agents that impart transgene-dependent incompatibility to plants. ZPT2-10 to provide agents that impart transgene-dependent incompatibility to plants incorporated by reference.

EXAMPLES

The present invention will be specifically described using Examples, but it is not to be construed as being limited thereto.

Example 1

Preparation of SK2:ZPT2-10 Fusion Gene

A DNA fragment (940 bp) comprising the nucleotide sequence of the potato SK2 chitinase gene promoter region was excised from plasmid pSK2/1 (Ficker, M. et al., Plant Mol. Biol. 35, 1997, 425-431) with XpaI and NcoI. The pSK2/1 was kindly provided by Dr. Richard D. Thompson (Max Planc Institute, Germany). Meanwhile, a NcoI-ZPT2-10:NOS-terminator fragment was obtained by PCR using:

an upstream primer (5'-CAT GCC ATG GAT CTT CTA CAA GAT-3'/SEQ ID NO: 3) designed so that the NcoI site is inserted in the upstream of the ATG initiation codon in the ZPT2-10-coding sequence;

an M13 (−20) primer (Stratagem) carried by a pUC19 vector; and as a template, a pUC-ZPT2-10-NT plasmid comprising in a pUC19 vector the ZPT2-10 cDNA (1,200 bp/SEQ ID NO:1) (Kubo, K. et al., Nucleic acids Res. 26, 1998, 608-615) and a NOS terminator sequence.

Then, the SK2 promoter fragment and the NcoI-ZPT2-10:NOS-terminator fragment were successively inserted into pBluescript SK+ to prepare SK2::ZPT2-10::NOS-terminator gene. The resulting gene was inserted into a pGreen 0029 binary vector (Hellens, R. P. et al., plant Mol. Biol. 42, 2000, 819-832) to obtain pGreen-SK2::ZPT2-10 (FIG. 1).

Example 2

Introduction of SK2:ZPT2-10 Fusion Gene into *Petunia* Cells

According to the description of Hellens et al. (Hellens, R. P. et al., Plant Mol. Biol. 42, 2000, 819-832), pGreen-SK2::ZPT2-10 was mixed with a pSoup plasmid, and transfected into the *Agrobacterium tumefaciens* strain gv3101 by an electroporation method. The resulting *Agrobacterium* transformants were introduced into *petunia* by the leaf disc method (Jorgensen, R. A. et al., Plant Mol. Biol. 31, 1996, 957-973).

Example 3

Analysis of Crossing Properties

Figure 2:
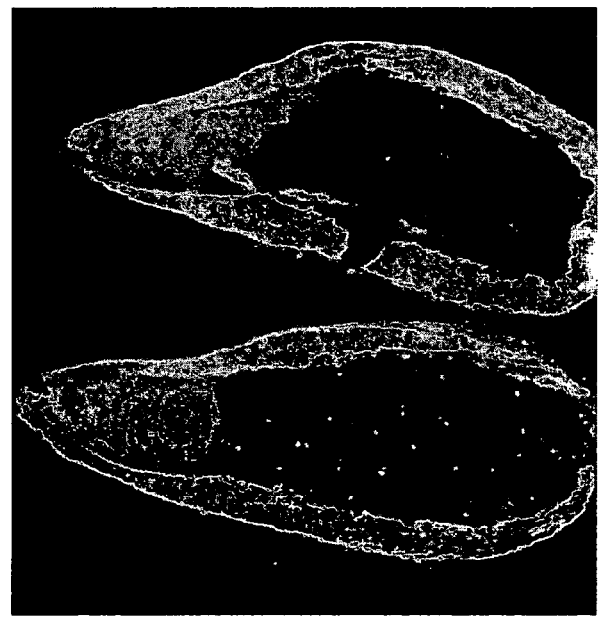
FIG. 2 is a set of photographs showing the TDI strain crossing property of a T0 generation. The fruition states in plants resulted from fertile mating (FIG. 2A) and infertile mating (FIG. 2B) are shown respectively.

Pollen was collected from the anthers in flowers of the above-described SK2::ZPT2-10 gene-introduced *petunia* one to two days after flowering. Self-pollination was then performed by pollinating stigmas (5 cm or higher) of emasculated buds (one day before flowering) in the same plants. As a result, all plants produced normal seeds. On the other hand, when pistils of a wild-type strain were pollinated with pollens of the SK2::ZPT2-10 gene-introduced *petunia*, and vice versa, no fruition was observed in any of the three independent transformation lines used (Table 1 and FIG. 2). Such a phenomenon is called transgene-dependent incompatibility (TDI), and strains with such a crossing property are called the TDI strain. In TDI-strain *petunias*, abnormality is not recognized in traits other than the crossing property.

Table 1: Analysis of Crossing Properties

TABLE 1

|  |  | ♂(POLLEN PARENTS) | | | | |
| --- | --- | --- | --- | --- | --- | --- |
|  |  | TDI-1 | TDI-2 | TDI-3 | NON-TDI | MWT |
| ♀(PISTIL PARENTS) | TDI-1 | 87 | 100 | 89 | 0 | 0 |
|  | TDI-2 | 100 | 100 | 85 | 0 | 0 |
|  | TDI-3 | 100 | 100 | 96 | 0 | 0 |
|  | NON-TDI | 0 | 0 | 0 | 100 | 100 |
|  | MWT | 0 | 0 | 0 | 100 | 100 |

FRUITION RATE (%)
n (POLLINATION TIME) = 4 to 20

Example 4

Inheritance of the TDI Trait

Figure 3:
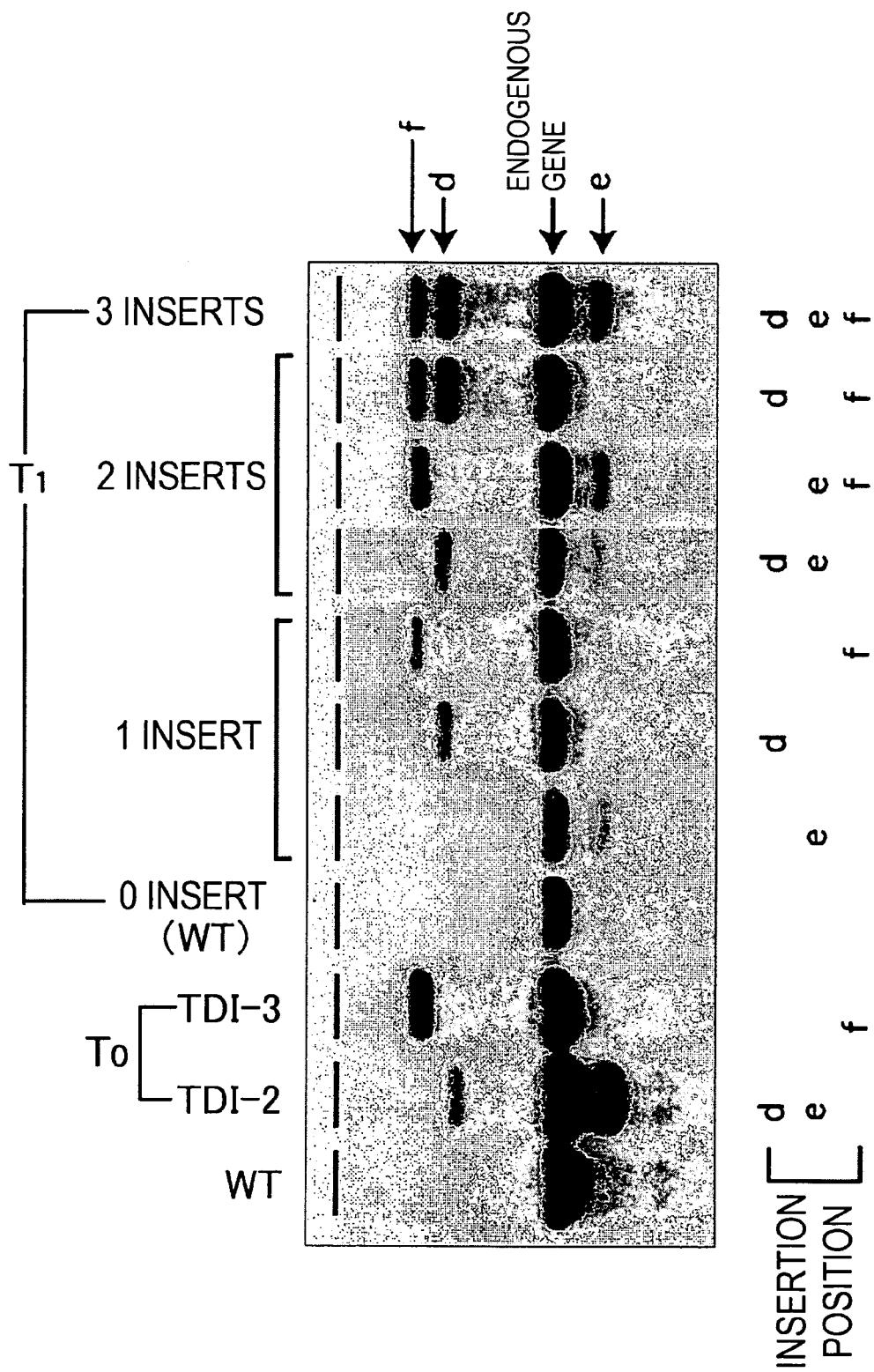
FIG. 3 is a photograph of the analysis of transgene inheritance in the T1 generation of a TDI strain. The genomic DNAs of T1 plants resulted from mating TDI-2 with TDI-3 were excised with HindIII, subjected to Southern hybridization using the ZPT2-10 cDNA as a probe, and examined for the presence of the SK2:ZPT2-10 transgene.

In order to obtain TDI strain T1 generation, T0 individuals of three independent TDI strains were mated with one another and seeds were obtained. The T1 generation was analyzed for its introduced genes and crossing properties, and the relationship between the gene that has been introduced and the observed crossing property was examined. In order to examine inheritance of the introduced SK2::ZPT2-10 gene, the presence of transgene-specific bands in genomic DNAs extracted from each individual was examined by Southern blot analysis (Sambrook, J. et al., Molecular Cloning: A Laboratory Manual, 2nd ed., Cold Spring Harbor Laboratory Press, 1989), using the ZPT2-10 cDNA as a probe. As a result, the T1 individuals were divided among those that have SK2::ZPT2-10 genes from both parents; those that have inherited the SK2::ZPT2-10 gene from one of the parents; and those that have not inherited the SK2::ZPT2-10 gene (FIG. 3). T1 individuals from the respective groups were propagated by the same crossing method described in Example 3, and their crossing properties were examined. The results showed that all T1 individuals comprising the SK2::ZPT2-10 gene inherited from TDI-strain parents are fertile like their parent individuals if self-propagated or mated with other TDI strains, and are infertile when mated with the wild-type strain (Table 2). On the other hand, individuals not comprising the SK2::ZPT2-10 gene, except one individual, produced seeds through either of the mating patterns, and exhibited entirely normal crossing properties. These results showed that the TDI property has a strong connection with the introduced SK2::ZPT2-10 gene, and is stably inherited by progenies.

Table 2: Inheritance of the TDI Trait

TABLE 2

| | | | | TDI♀ × TDI♂ | PISTIL PARENTS | | | POLLEN PARENTS | | |
| --- | --- | --- | --- | --- | --- | --- | --- | --- | --- | --- |
| | | | | (SELF-POLLINATION) | TDI♀ × WT♂ | TDI♀ × ANOTHER STRAIN TDI♂ | | WT♀ × TDI♂ | TDI♂ × ANOTHER STRAIN TDI♀ | |
| | | PLANT NAMES | TRANS-GENES | FRUITION RATE (%) | FRUITION RATE (%) | FRUITION RATE (%) | ♂MATING SPEICES | FRUITION RATE (%) | FRUITION RATE (%) | ♀MATING SPEICES |
| | | MWT | — | 100 | | | | | | |
| T0 | | TDI-1 | abcg | 87 | 0 | 100 | TDI-2 | 0 | 100 | TDI-2 |
| | | TDI-2 | de | 100 | 0 | 100 | TDI-1 | 0 | 100 | TDI-3 |
| | | TDI-3 | f | 100 | 0 | 100 | TDI-2 | 0 | 100 | TDI-2 |

TABLE 2-continued

FERTILITY OF T0 AND T1 PLANTS

| | | | | TDI♀ × TDI♂ (SELF-POLLINATION) FRUITION RATE (%) | PISTIL PARENTS | | | POLLEN PARENTS | | |
|---|---|---|---|---|---|---|---|---|---|---|
| | | | | | TDI♀ × WT♂ FRUITION RATE (%) | TDI♀ × ANOTHER STRAIN TDI♂ FRUITION RATE (%) | ♂ MATING SPEICES | WT♀ × TDI♂ FRUITION RATE (%) | TDI♂ × ANOTHER STRAIN TDI♀ FRUITION RATE (%) | ♀ MATING SPEICES |
| | | PLANT NAMES | TRANS-GENES | | | | | | | |
| | T1 | 28a | a | 88 | 0 | 100 | 93f | 0 | | |
| | | 33a | a | 86 | 20 | 100 | 15d | 0 | | |
| | | 32b | b | 100 | 0 | | | 0 | | |
| | | 36b | b | 100 | 25 | 100 | 3df | 0 | 100 | 25cf |
| | | 72b | b | 100 | 0 | 100 | 31f | 22 | 100 | 93f |
| | | 111c | c | 92 | 0 | | | 0 | 100 | 25cf |
| | | 15d | d | 100 | 6 | 100 | 31f | 0 | 100 | 33a |
| | | 101e | e | 100 | 0 | | | 0 | 100 | 33a |
| | | 104e | e | 100 | 0 | | | 0 | | |
| | | 17f | f | 100 | 0 | | | 0 | | |
| | | 31f | f | 100 | 0 | 100 | 11ef | 0 | 100 | 72b |
| | | 93f | f | 100 | 0 | 100 | 72b | 0 | 100 | 28a |
| | | 25cf | cf | 100 | 0 | 100 | 111c | 0 | | |
| | | 44cf | cf | 100 | 0 | 100 | 31f | 0 | 100 | 25cf |
| | | 3df | df | 100 | 0 | | | 0 | 100 | 36b |
| | | 11ef | ef | 100 | 0 | | | 43 | 100 | 31f |
| T1 (REVERTANT) | T1 | 14 wt | — | 100 | 85 | | | 80 | | |
| | | 113 wt | — | 100 | 78 | | | 100 | | |
| | | B6 wt* | — | 69 | 57 | | | 0 | | |
| | | NON-TDI-4 | (1 COPY) | 100 | 100 | 0 | 1T0 | 100 | 0 | 1T0 |
| | | | | (n = 3~22) | (n = 4~16) | (n = 2~6) | | (n = 2~8) | (n = 2~8) | |

Example 5

Figure 4:
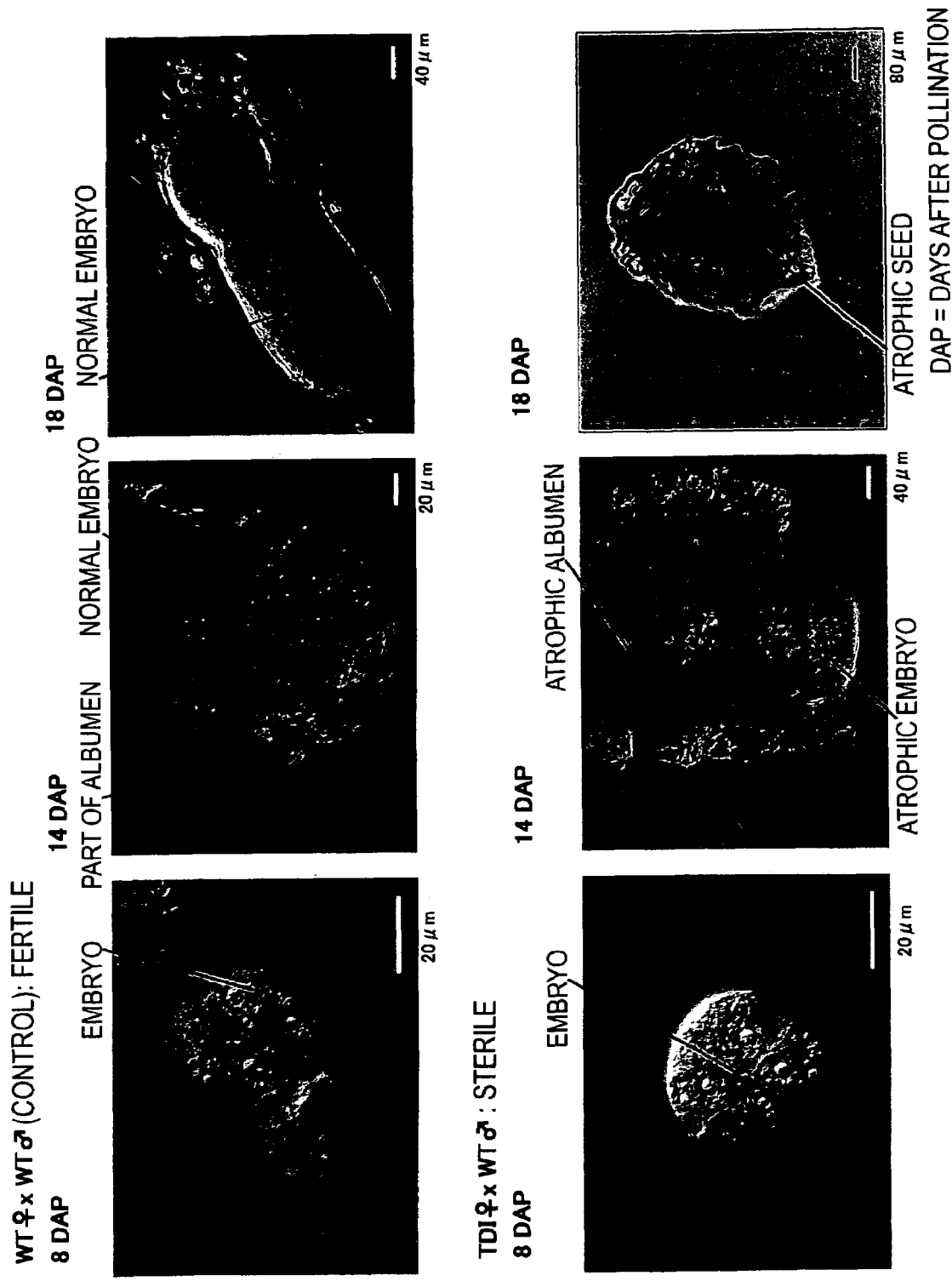
FIG. 4 is a photograph showing that the TDI infertility is caused by embryogenesis arrest. In infertile mating (TDI (female)×WT (male)), embryogenesis is arrested between a spherical-shaped embryo and a heart-shaped embryo.

The post-pollination stage, at which abnormalities responsible for the infertility resulted from incompatible pollination between TDI individuals and wild-type plants occurred, was examined. The results show that the inhibition was not seen during the pollen tube elongation process and that pollen tubes had reached ovules normally. However, embryogenesis was found to discontinue after fecundation, and embryos died as a result of this (FIG. 4).

What is claimed is:

1. A method for improving the plant crossing properties of a transgenic plant by providing a plant with transgene-dependent incompatibility, wherein the method comprises the steps of:
- (i) introducing a transgene into a plant cell, said transgene comprising a DNA or a vector comprising the DNA, wherein said DNA comprises:
  - (a) a DNA encoding a protein comprising the amino acid sequence of SEQ ID NO: 2; or
  - (b) a DNA comprising the coding region of the nucleotide sequence of SEQ ID NO: 1,
- (ii) regenerating a transformed plant from the plant cell into which the DNA or the vector is introduced in step (i),
- (iii) expressing the DNA conferring transgene-dependent incompatibility in said transformed plant of step (ii), and
- (iv) confirming the transgene-dependent incompatibility of the transformed plant by observing that the transformed plant produces normal seeds when self-pollinated, but fails to reach fruition when pollination occurs through mating with a wild-type strain, thereby effectively preventing the transformed plant from mating with wild-type and native species and spreading recombinant genes into the environment.

2. The method of claim 1, wherein the DNA of step (i) is a DNA encoding a protein comprising the amino acid sequence of SEQ ID NO: 2.

3. The method of claim 1, wherein the DNA of step (i) is a DNA comprising the coding region of the nucleotide sequence of SEQ ID NO: 1.

* * * * *

```
                        SEQUENCE LISTING

<160> NUMBER OF SEQ ID NOS: 3

<210> SEQ ID NO 1
<211> LENGTH: 1146
<212> TYPE: DNA
<213> ORGANISM: Petunia hybrida

<400> SEQUENCE: 1
atggatcttc tacaagatag agagagtgaa accgagtcat taccatatcc aacacaatgt      60
aaacgataca agcggatcat aaactcaaga atctcagata cacattacaa tcagttttta     120
tcattagaac gacgacgaca acaacaacaa caacagtatg gaaagattac agagtttcca     180
tttgttgagt ctgagccagt gagttcaatt tcagacactt caccagatga agacgttgcg     240
aactgcttga tgatgttatc tagagataag tggatgacac aagaaaatga agttatcgac     300
aatagtgcta gctatgatga agatgtaaaa acagaggact ctgtagttgt taaagtgaca     360
acgactagga ggggtagagg taagtacata tgtgaaacat gtaacaaagt ttttagatct     420
tatcaagcac ttggtggtca tagagcaagt cacaagaaga ttaaagtctc aattaatgaa     480
acaaaaaaca atggaaatgt agaaagtgag gttcaaaagg ataaaataca tgaatgtcct     540
gtttgttaca gagtattttc atcaggacaa gctcttggtg gacacaagag gtcacatggt     600
```

-continued

```
attggtgtag cagccacaaa tgtgagtctt tcaacaaaaa ttgtatcatc aagaattagt    660
ggaactatga tagatctcaa tattcctgct acattggagg atgatgagat tagtcaaatt    720
gaggtttctg cagtttctga tgatgaattt gtcaacccct gagtcgaagg tctatcagaa    780 agaaccctg taggagtaag atctgcgtac atctcaccct cctcagaatt catctgtagg     840
attatatcag gtacattgtt attgctgttg aatttgtcat ccccatcaag cactgaaatg    900
atgttattct tagagttaat gaaactcaag aattataggg aaagttttgt tcttattttg    960
acctttttaa gttcttaggt atggaactaa ggaaattgat cagtactttt tcttggaaaa   1020
cattagcact ttccaagcta tactcattga atatctgaat agttttgact gtaattaaat   1080
tttccaactc tgctttgttt atgttacagc ttattaatat catctattaa tttaactctg   1140
ttctgt                                                              1146
```

<210> SEQ ID NO 2
<211> LENGTH: 253
<212> TYPE: PRT
<213> ORGANISM: Petunia hybrida

<400> SEQUENCE: 2

```
Met Asp Leu Leu Gln Asp Arg Glu Ser Glu Thr Glu Ser Leu Pro Tyr
1               5                   10                  15

Pro Thr Gln Cys Lys Arg Tyr Lys Arg Ile Ile Asn Ser Arg Ile Ser
            20                  25                  30

Asp Thr His Tyr Asn Gln Phe Leu Ser Leu Glu Arg Arg Arg Gln Gln
        35                  40                  45

Gln Gln Gln Gln Tyr Gly Lys Ile Thr Glu Phe Pro Phe Val Glu Ser
    50                  55                  60

Glu Pro Val Ser Ser Ile Ser Asp Thr Ser Pro Asp Glu Asp Val Ala
65                  70                  75                  80

Asn Cys Leu Met Met Leu Ser Arg Asp Lys Trp Met Thr Gln Glu Asn
                85                  90                  95

Glu Val Ile Asp Asn Ser Ala Ser Tyr Asp Glu Asp Val Lys Thr Glu
            100                 105                 110

Asp Ser Val Val Val Lys Val Thr Thr Thr Arg Arg Gly Arg Gly Lys
        115                 120                 125

Tyr Ile Cys Glu Thr Cys Asn Lys Val Phe Arg Ser Tyr Gln Ala Leu
    130                 135                 140

Gly Gly His Arg Ala Ser His Lys Lys Ile Lys Val Ser Ile Asn Glu
145                 150                 155                 160

Thr Lys Asn Asn Gly Asn Val Glu Ser Glu Val Gln Lys Asp Lys Ile
                165                 170                 175

His Glu Cys Pro Val Cys Tyr Arg Val Phe Ser Ser Gly Gln Ala Leu
            180                 185                 190

Gly Gly His Lys Arg Ser His Gly Ile Gly Val Ala Ala Thr Asn Val
        195                 200                 205

Ser Leu Ser Thr Lys Ile Val Ser Ser Arg Ile Ser Gly Thr Met Ile
    210                 215                 220

Asp Leu Asn Ile Pro Ala Thr Leu Glu Asp Glu Ile Ser Gln Ile
225                 230                 235                 240

Glu Val Ser Ala Val Ser Asp Asp Glu Phe Val Asn Pro
                245                 250
```

```
-continued

<210> SEQ ID NO 3
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 3
catgccatgg atcttctaca agat                                          24
```